United States Patent [19]

Di Benedetto et al.

[11] Patent Number: 4,531,398

[45] Date of Patent: Jul. 30, 1985

[54] CALIBRATION SYSTEM FOR GAS ANALYZERS

[75] Inventors: Dominique Di Benedetto; Jean-Claude Marchand, both of Saint-Etienne, France

[73] Assignee: Association pour la Recherche et le Devolloppement des Methodes et Processus Industriels-A.R.M.I.N.E.S., Paris, France

[21] Appl. No.: 515,034

[22] Filed: Jul. 18, 1983

[30] Foreign Application Priority Data

Jul. 27, 1982 [FR] France .................. 82 13104

[51] Int. Cl.³ .................. G01D 18/00; G01M 19/00
[52] U.S. Cl. .................. 73/1 G
[58] Field of Search .................. 73/1 G

[56] References Cited

U.S. PATENT DOCUMENTS

| | | | |
|---|---|---|---|
| 3,521,865 | 7/1970 | Kertzman | 73/1 G X |
| 3,533,272 | 10/1970 | Dahms | 73/1 G |
| 3,618,911 | 11/1971 | Martin | 73/1 G X |
| 3,689,038 | 9/1972 | Martin | 285/338 X |
| 3,776,023 | 12/1973 | Budd et al. | 73/1 R |
| 3,788,545 | 1/1974 | Budd et al. | 239/34 |
| 3,824,836 | 7/1974 | Lyshkow | 73/1 G |
| 3,948,604 | 4/1976 | Hoppesch | 73/1 G X |
| 4,036,915 | 7/1977 | Lucero et al. | 73/1 G X |
| 4,164,861 | 8/1979 | Schelereth et al. | 73/1 G |
| 4,209,300 | 6/1980 | Thibault | 73/1 G X |
| 4,279,142 | 6/1981 | McIntyre | 73/1 G |

FOREIGN PATENT DOCUMENTS

| | | | |
|---|---|---|---|
| 253243 | 3/1967 | Austria | 73/1 G |
| 173740 | 10/1982 | Japan | 73/1 G |
| 748167 | 7/1980 | U.S.S.R. | 73/1 G |

OTHER PUBLICATIONS

Scaringelli et al., excerpt from "Analytical Chemistry", vol. 42, No. 8, Jul. 1970, pp. 871-876.
"Advances in Instrumentation", vol. 31, No. 3 (1976), Design Criteria for a Portable Gas Phase Titration Calibration System, p. 710, lines 1-6 and FIGS. 3 and 4, Jerry Clemons et al., (6 sheets).
Hughes et al., article from "Advances in Instrumentation", vol. 29, No. 3 (1974), entitled Development of Standard Reference Materials for Air Quality Measurement, p. 704, lines 1-13 (13 sheets).
"Generator for Producing Trace Vapor Concentrations of 2,4,6-Trinitrotoluene, 2,4-Dinitrotoluene, and Ethylene Glycol Dinitrate for Calibrating Explosives Vapor Detectors"; *Analytical Chemistry*, vol. 48, No. 11, Sep. 1976, pp. 1632-1637, Peter A. Pella.

Primary Examiner—Stewart J. Levy
Assistant Examiner—Tom Noland
Attorney, Agent, or Firm—Sandler & Greenblum

[57] ABSTRACT

A calibration system is provided for gas analyzers, and particularly for apparatus for measuring atmospheric pollution and for detecting gaseous pollutants. The device comprises a tight permeation chamber connected to a source of a gaseous pollutant or a plurality of chemically compatible gaseous pollutants, e.g., $SO_2$, $NO$ or $CH_4$. A tube formed from a material which is permeable to the gaseous pollutant(s) extends across the chamber, one end of the tube being connected to a source of pressurized pure vector gas and the other end of the tube communicating with a mixer which is itself connected to a source of dilution zero air. Apparatus is also provided for regulating temperature to maintain a predetermined constant temperature within the permeation chamber.

5 Claims, 4 Drawing Figures

CALIBRATION SYSTEM FOR GAS ANALYZERS

BACKGROUND OF THE INVENTION

The present invention relates to a calibration system for gas analyzers, particularly for apparatus measuring atmospheric pollution.

For studying atmospheric pollution (gaseous pollutants, fumes, particles), measuring networks are used, constituted by stations distributed over a given territory. In these stations, gas analyzers permanently measure the contents of the pollutants studied. In order to obtain reliable results of analysis, it is necessary periodically to calibrate the gas analyzers with the gaseous pollutants which are monitored. Furthermore it is also necessary to ensure the physical intercalibration of the analyzing apparatus, i.e. to ensure that the pollutant and air standards and the sampled air are taken in the measuring station under the same conditions.

Calibration systems are already known which use liquefied pollutant gases contained in permeation tubes generally made of "Teflon". One of the walls of this tube is generally scavenged by "zero air", into air containing no pollutant, or another gas such as nitrogen, at a constant rate of flow, the zero air or nitrogen passing around the permeation tube. Because the pressure of the liquid pollutant contained within the permeation tube is equal to the saturating vapour pressure, and because the partial pressure of the pollutant in the zero air or the nitrogen which passes about the permeation tube is zero, the existence of a pollutant pressure gradient on either side of the wall of the tube is created, such gradient causing the pollutant(s) to diffuse through the wall of the tube from the interior of the tube towards the exterior of the tube. This pressure gradient remaining constant, the rate of diffusion through the tube remains constant.

Such a system incorporating a liquid permeation tube presents a certain number of drawbacks. In the first place, the pressure of the pollutant gas increases exponentially with the temperature, this being detrimental to maintaining a constant concentration. Furthermore, the saturating vapour pressure inside the liquid permeation tube remains fixed, which does not enable the rate of permeation to be varied. In addition, these systems effect calibration only with the gases which are liquefiable in conventional permeation tubes, such as $SO_2$, $NO_2$, $H_2S$. The temperature of permeation at which the tube containing the liquefied pollutant gases maintained, is relatively low in order not to create too high pressures inside the tube. By reason of these relatively low temperatures, the variation with respect to ambient temperature is relatively small, the consequence of which is that the temperature regulating system does not always operate under good conditions.

SUMMARY OF THE INVENTION

It is essentially an object of the present invention to overcome these drawbacks by providing an apparatus of particularly simple design which effects reliable calibration by means of a large number of gaseous pollutants. To this end, this calibration system for gas analyzers particularly for apparatus for measuring atmospheric pollution detecting gaseous pollutant, comprises a tight permeation chamber connected to a source of a gaseous pollutant or a plurality of chemically compatible gaseous pollutants such as $SO_2$, NO, or $CH_4$, a tube made of a material permeable to the pollutant gas extending across this chamber, one end of this tube being connected to a source of pure vector gas under pressure and its other end communicating with a mixer itself connected to a source of dilution zero air, and means for regulating the temperature to maintain a predetermined constant temperature inside the permeation chamber.

The gaseous permeation tube housed in the permeation chamber is preferably made of "Teflon", in the case of an aggressive gaseous pollutant, or silicon in the case of a less aggressive gaseous pollutant, such as $SO_2$, $NH_4$, or of any other polymer presenting advantageous characteristics for the permeation technique.

The calibration system according to the invention offers various advantages over the known apparatus. The system can be emptied and refilled as desired with any gas compatible with the polymer used for the permeation tube, this allowing unlimited re-use. As gaseous pollutants are used, the rate of permeation may be regulated as desired by adjusting the pressure of the gaseous pollutant and possibly the number of holes offered for diffusion, in the case of the permeation tube being fitted on a perforated steel tube.

The apparatus according to the invention may also use a mixture of several compatible gaseous pollutants. All gases such as NO, CO, $CH_4$, etc... can therefore be diffused, and not solely those which are liquefiable in the conventional permeation tubes such as $SO_2$, $NO_2$, $H_2S$. As the gaseous pollutant is outside the permeation tube where diffusion takes place and as the gas entraining the pollutant licks (contacts and mixes with) the pollutant inside the tube, a symmetry of revolution for diffusion and consequently the total absence of unemployed volume detrimental to the constancy of the rate of diffusion are obtained.

The permeation device may work with mixtures of chemically compatible gases. All these gases diffuse together and follow the same destiny. Consequently an abnormality on one of the constituents of the mixture will be found on the others and, inversely, correct operation on one of the gaseous ensures that the operation for the other gases must be correct. In this way the calibrator is very safe, as the system is "blind". However, the permeation temperature, the rate of flow of air and the filling pressure of the pollutant are monitored. Moreover, the use of titration in gaseous phase, of which the reaction is rapid and complete, due to the rapid and high concentration of $O_3$ and NO in the reaction chamber, further strengthens the interdependence of all the pollutants.

The permeation temperature is preferably set at 64° C., this ensuring that, whatever the place of use, the variation between the ambient temperature and that of the permeation device will always be sufficient for the regulation of temperature (from a D.C. source at 12 V) to operate under good conditions. On the contrary, this is not the case of the known apparatus using liquid permeation tubes which cannot rise to such a temperature due to the excessively high pressures attained by the pollutants within the permeation tube.

A further advantage of the system according to the invention is that it does not require a cylinder of NO, since this gas is obtained by permeation within the system and, in addition, the rate of flow of zero air or of nitrogen scavenging the tube does not need to be regulated: it must simply ensure that the partial pressure of the pollutant within the tube is zero for the rate of diffusion to remain constant. As the nitrogen constituting the vector gas containing the pollutants represents less than 1% of the final rate of flow, the final concentration of the or each pollutant at the outlet of the system is therefore independent of the rate of flow of nitrogen. On the contrary for the systems known at present, NO is obtained directly from a cylinder at 100 ppm (for example) nd consequently the rate of flow of this cylinder must be carried fully regulated so that the final concentration remains constant.

The dilution gas must be a zero air not containing the pollutants produced by the system. Now, it is not known how to obtain an air having a zero content of NO by conventional adsorption on active carbon or a molecular sieve. The known systems therefore do not guarantee a zero air. On the contrary, in the apparatus according to the invention, a zero air in NO, $NO_2$, $SO_2$ and $O_3$ is obtained by passing the air drawn in by a pump around an ozone generator: $O_3$ thus produced then completely oxidizes into $NO_2$ and then $SO_2$, $O_3$ and NO which are possibly present in the ambient air are then fixed on active carbon, NO having been previously converted into $NO_2$.

Another advantage of the system according to the invention is that the life duration of a filling may attain several years and, furthermore, this system is always ready for operation since it remains operational during transport (being supplied from a 12 V battery of a vehicle) and since, with its internal batteries, it is self-sufficient for thirty hours.

BRIEF DESCRIPTION OF THE DRAWINGS

The invention will be more readily understood on reading the following description with reference to the accompanying drawings, in which.

DESCRIPTION OF THE PREFERRED EMBODIMENTS

Figure 1:
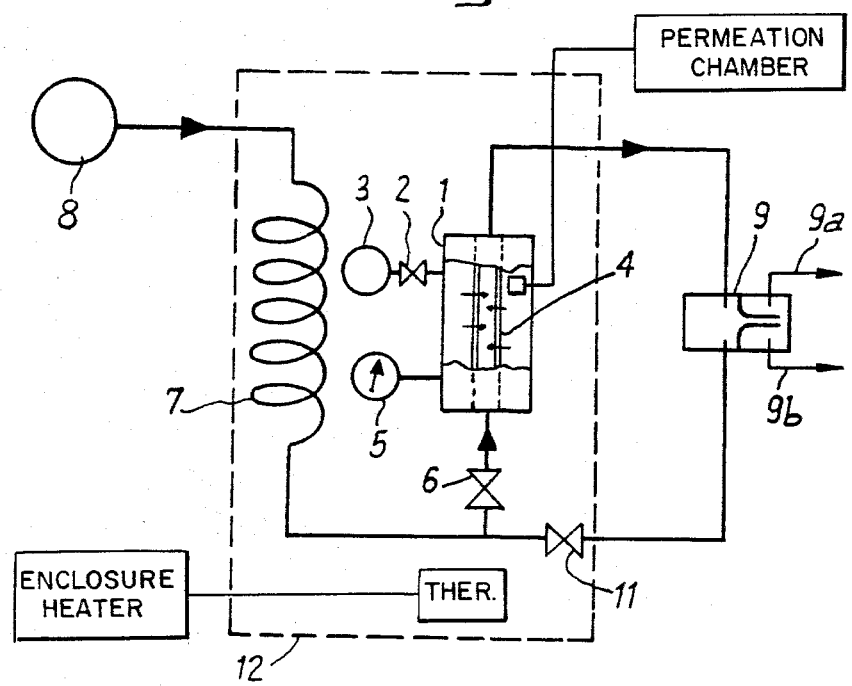
FIG. 1 is a circuit diagram of a calibration system for gas analyzers according to the invention, using a gaseous permeation tube.

Referring now to the drawings, the calibration system according to the invention, of which the principle is illustrated by the diagram of FIG. 1, comprises a tight permeation chamber 1 which is connected, by a stop valve 2, to a source 3 of at least one pollutant gas. This permeation chamber 1 has a permeation tube 4 made of a material permeable to the pollutant gas, such as silicon or other polymers, passing right through it. The pressure of the pollutant gas in the chamber 1 is indicated by a pressure gauge 5. One end of the permeation tube 4 is connected, via a valve 6 and a pipe coil 7, to a source 8 of a vector gas which may be "zero" air, i.e. pure of any pollutant gas such as NO, $NO_2$, $SO_2$, $O_3$, or nitrogen. The other end of the permeation tube 4 is connected to a mixer 9 in which a dilution zero air flow is also directly introduced through a valve 11. The permeation chamber 1 as well as the coil 7 are housed in an enclosure 12 of which the temperature is regulated so as to be maintained constant, for example equal to 64° C.

From the foregoing description, it is seen that the vector gas ("zero" air or nitrogen) flows through the permeation tube 4, at a rate of flow adjustable by the valve 6. Furthermore, the or each pollutant gas is introduced into the permeation chamber 1, all around the permeation tube 4, at an adjustable partial pressure controlled by means of the pressure gauge 5. Inside the permeation tube 4, the partial pressure of the pollutant gas is virtually zero. On both sides of the wall of the permeation tube 4, there is therefore a gradient of concentration. If this gradient is maintained constant, i.e. if the partial pressure of the pollutant gas in the chamber 1 is maintained constant around tube 4, the speed of diffusion, i.e. the quantity of pollutant which passes through the wall of the tube 4 per unit of time, is constant. Consequently, a constant, low concentration of the pollutant in the "zero" air or nitrogen at the outlet of the permeation tube 4 is obtained. The final concentration is obtained due to a diversion on the zero air circuit, the rate of flow of zero air introduced directly into the mixer 9 being regulated by means of valve 11. This mixer 9 is necessary for good homogenization of the air+pollutant mixture which leaves towards the user via a pipe 9a. Another outlet pipe 9b is provided to ensure the outlet of the excess of the mixture thus guaranteeing that the pressure inside the mixer 9 remains equal to atmospheric pressure. Consequently, the gas analyzer which is subsequently connected to the system according to the invention, takes the gaseous standard under the same pneumatic conditions as the samples of the atmosphere.

Figure 3:
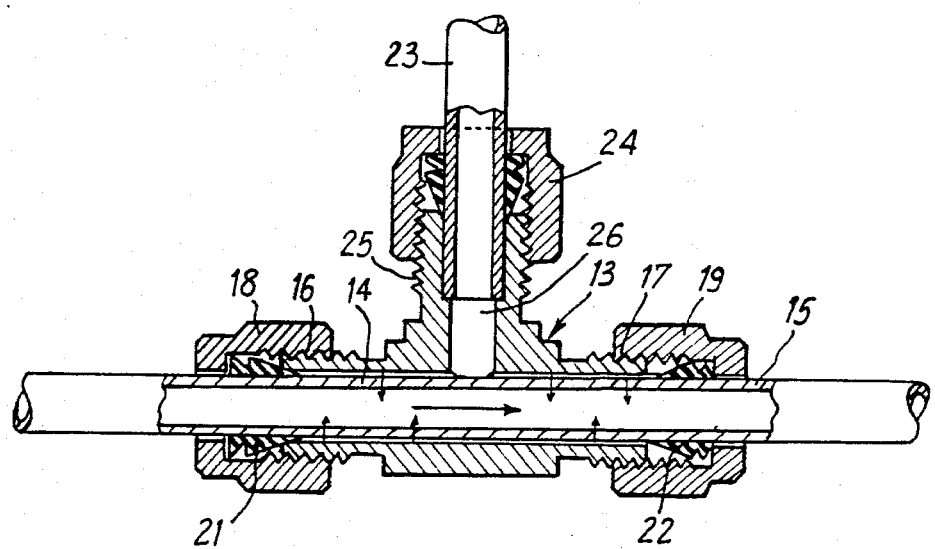
FIG. 3 is a view in axial section of a gaseous permeation tee.
Figure 2:
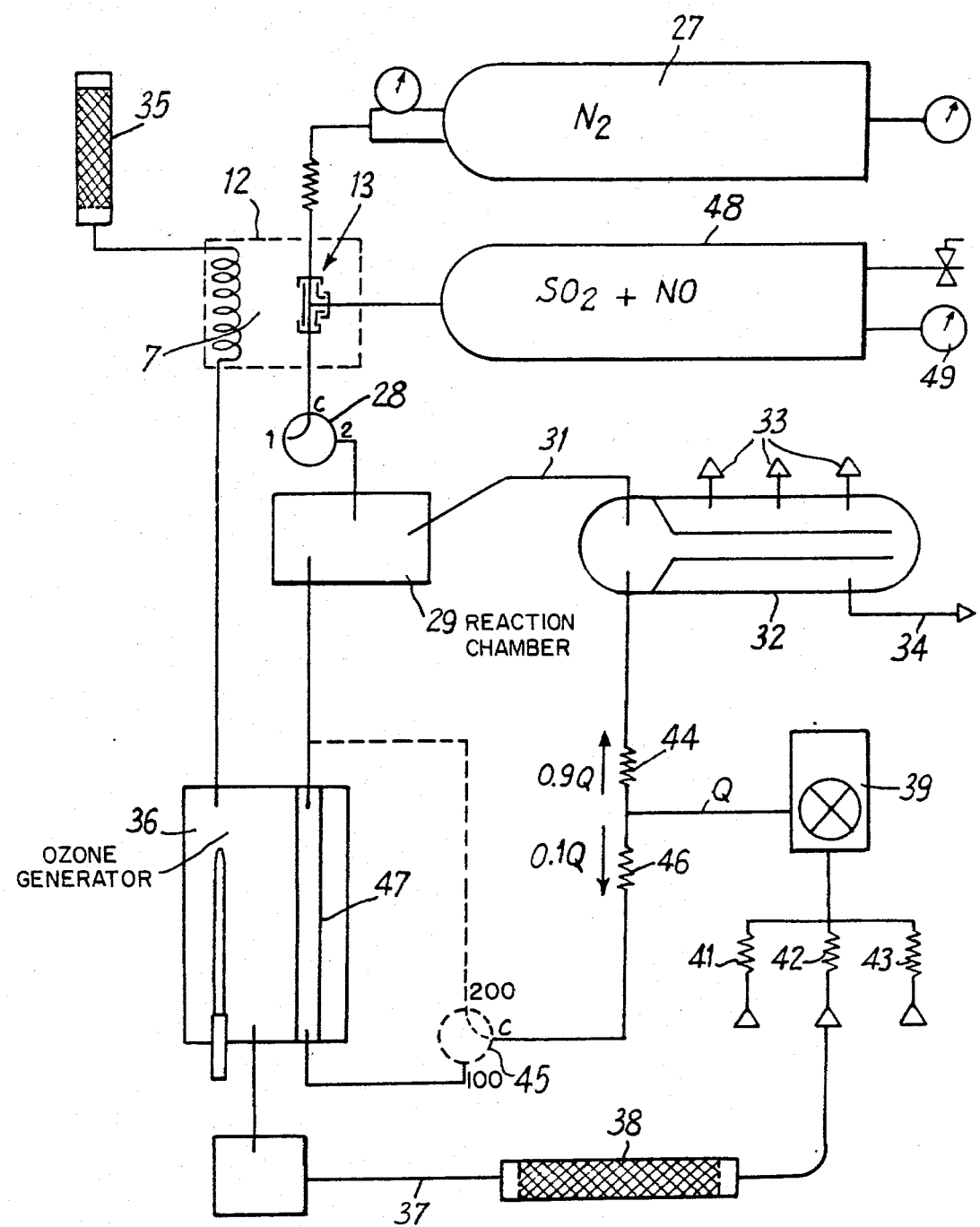
FIG. 2 is a detailed diagram of an embodiment of the calibration system according to the invention.

A particular embodiment of the invention will now be described with reference more especially to FIG. 2, the elements of this Figure similar to those of FIG. 1 being given the same references. In this embodiment of the invention, the permeation chamber is constituted by a tee 13 shown in detail in FIG. 3. This tee comprises a body which is pierced right through with a bore 14 through which extends a permeation tube 15 made for example of "Teflon". The body of the tee 13 is provided at the two ends of the bore 14 with threaded unions 16, 17 on which are screwed respective nuts 18 and 19 through which the permeation tube 15 passes. These nuts ensure blockage of the tube 15 in the unions 16, 17 via respective conical rings 21, 22. This type of union is known under the name of "Swagelock".

The outer diameter of the permeation tube 15 is smaller than the diameter of the bore 14 so as to define with the wall of the latter a chamber in which the gaseous pollutant is introduced. This pollutant is supplied through a pipe 23 which is fixed, by means of a nut 24, to a threaded union 25 surrounding a transverse conduit 26 opening out perpendicularly into bore 14 at the centre thereof.

The permeation tube 15 is connected, at one of its ends, to a nitrogen cylinder 27 (FIG. 2), whilst its other end is connected to a three-way valve 28. This valve ensures communication with a reaction chamber 29 which is connected, via a pipe 31, to a sampling mixer 32. This mixer 32 is provided with a plurality of outlet connectors 33 adapted to be connected to the gas analyzers, as well as with a pipe 34 for the evacuation of excess of the mixture.

The atmospheric air is drawn through a filter 35 which is connected to one end of the coil 7 housed, with the permeation tee 13, inside the heat-regulated enclosure. The coil 7 is in turn connected to a nitrogen generator 36 of which the interior communicates, via a pipe 37 on which is connected an active charcoal filter 38, with the suction orifice of a pump 39. Elements 41, 42, 43 introducing variable pressure drops are connected to the intake orifice of the pump 39 to make it possible to set three different rates of flow of this pump, namely 78 l/hr., 135 l/hr. and 335 l/hr. for example. The delivery orifice of pump 39 is connected on the one hand to the sampling mixer 32, through a pressure drop element 44, and on the other hand to a threeway valve 45, via another pressure drop element 46. The rate of flow Q of zero gas furnished by the pump 39 is divided into two, namely a relatively high rate of flow (for example 0.9 Q) directed directly towards the mixer 32 and on the other hand a lower rate of flow (for example 0.1 Q) directed towards the three-way valve 45. This low rate of flow may be directed by this valve, in a first position thereof, so that it passes, as vector gas, through a quartz tube 47 extending across the ozone generator 36 and communicating, at its opposite end, with the reaction chamber 29. The ozone generator creates ozone in a well known manner within quartz tube 47 by passing ultraviolet light through the quartz, which is permeable or transparent to such light, so that the light will interact with the oxygen in the tube provided from the ambient air to form ozone. In a second position of the valve 45, the ozone generator 36 is shortcircuited and the flow of zero air is directed directly towards the reaction chamber 29. References 100 and 200 in FIG. 2 represent the first and second positions of the three-way valve 45, respectfully.

The or each pollutant gas is contained in one large-volume cell 48 which is connected to the permeation tee 13 by pipe 23. This cell 48, of which the pressure is indicated by a pressure gauge 49, may contain, for example, $SO_2$, $NO$, $CH_4$, $C_3H_8$, etc . . . .

The heat-regulated enclosure 12 is maintained at an appropriate temperature, of the order of 64° C. The temperature of the heat-regulated enclosure 12 is maintained constant by an electrical regulation circuit which may be supplied either from an A.C. source, in a station, or from a portable accumulator incorporated in the system.

The vector gas furnished to the permeation chamber 13 is constituted by nitrogen contained in cylinder 27, the nitrogen being furnished at a very low rate of flow. This rate of flow does not need to be regulated since the speed of permeation does not depend on the rate of flow of the nitrogen or the zero air, provided that the partial pressure of the gaseous pollutant of the vector gas is zero and that the rate of flow of the vector gas is very low with respect to the final rate of flow obtained at mixer 32. In fact, the rate of flow of nitrogen in the permeation chamber 13 is less than one hundredth of the rate of flow of dilution gas furnished by the pump 39 to the mixer 32.

The ambient air drawn in by pump 39 passes onto the ozone generator 36 in order to oxidize the NO of the ambient air into $NO_2$: under these conditions, $NO_2$ and the excess of ozone are adsorbed on the active charcoal filter 38 as well as $SO_2$ or other pollutants adsorbable on active charcoal.

The pump 39 thus draws in the zero air, whose rate of flow may be regulated by the pressure drop elements 41, 42, 43, this zero air not containing any pollutant such as NO, $SO_2$, $NO_3$, $NO_2$.

Thanks to the rate of flow used and to the sampling mixer 32, several gas analyzers may be supplied at the same time, particularly ozone and nitrogen oxide analyzers, in order to verify correct functioning of the titration in gaseous phase.

The three-way valve 45 makes it possible to use, or not, titration in gaseous phase.

Figure 4:
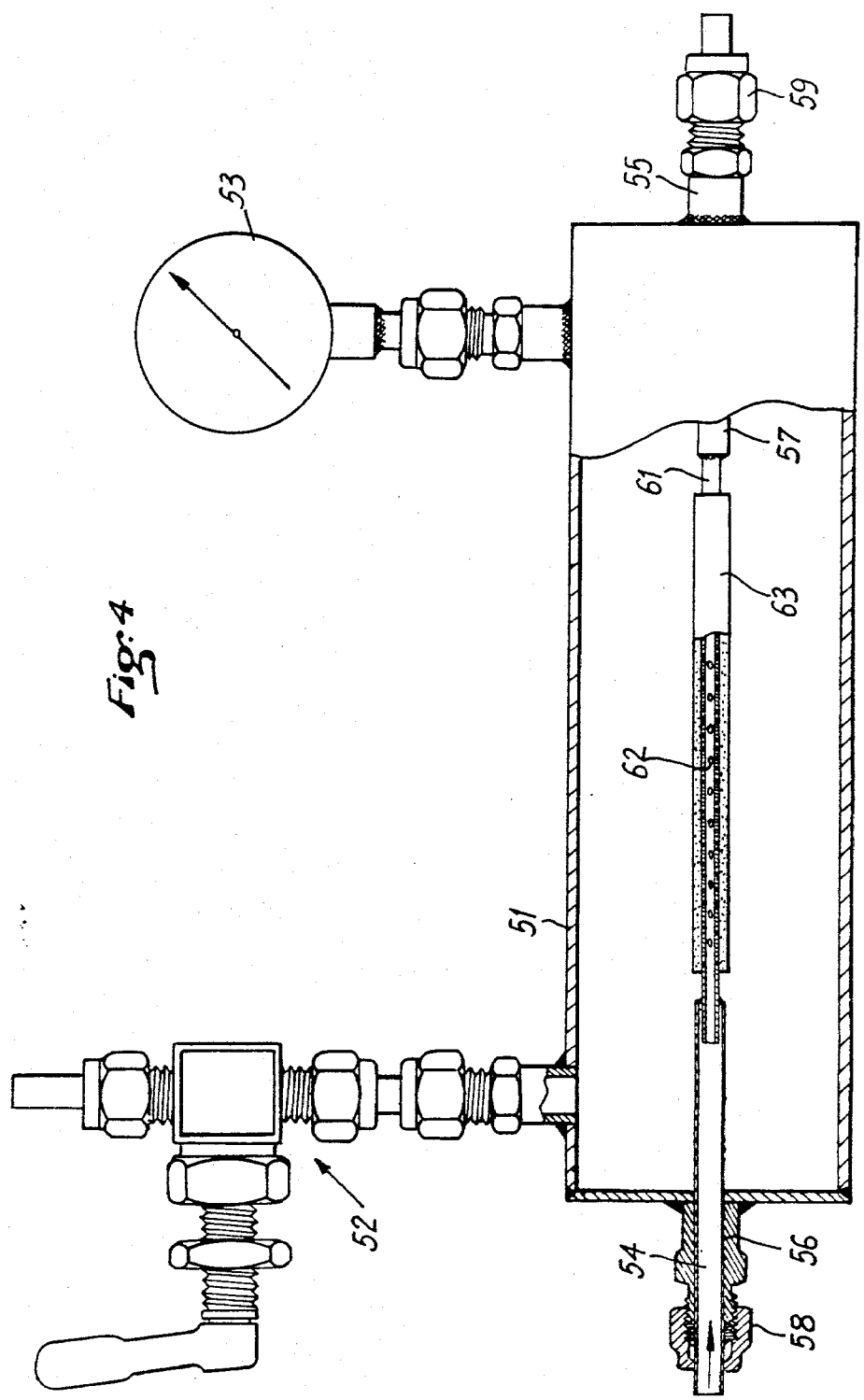
FIG. 4 is a view in axial section, partly in elevation, of a gaseous permeation cell.

With reference more particularly to FIG. 4, a nonlimiting example of a gaseous permeation cell which may be used in particular when the gaseous pollutant is constituted by sulfuretted hydrogen, will now be described. This cell comprises a hermetically closed cylindrical chamber 51 connected, by a stop valve 52, to a source of gaseous pollutant (sulfuretted hydrogen), the pressure in the chamber 51 being indicated by a pressure gauge 53. This cylindrical chamber 51 bears, on its two front faces, inlet and outlet unions 54 and 55 through which pass respective metal tubes 56, 57 which are blocked by means of nuts 58, 59. The two tubes 56, 57 extend coaxially inside the cylindrical chamber 51 and are welded, at their ends, to an intermediate tube 61 of smaller diameter, made of stainless steel. This tube is pierced, over a part of its length, by a certain number of holes 62. Furthermore, a permeation tube 63 is fitted on the perforated tube 61. In this way, the gaseous pollutant which is under pressure inside the cylindrical chamber 51, may diffuse through the permeation tube 63 which is made of silicon or another polymer, and may pass through the holes 62 in the stainless steel inner tube 61. The gaseous pollutant thus passes in the vector gas which traverses the permeation chamber 51 from left to right, through the tubes 56, 61, 57, the rate of permeation being a function of the gaseous pollutant as well as of the number of perforated holes in tube 61. To regulate this rate of permeation, the pressure of the gaseous pollutant in the chamber 51 or possibly the number of holes of the perforated tube 61 may be varied.

What is claimed is:

1. A calibration system adapted for use with gas analyzers, and particularly for use with apparatus for measuring atmospheric pollution and for detecting gaseous pollutants, said system comprising:
    (a) a sealed permeation chamber and a source of at least one gaseous pollutant connected to said permeation chamber;
    (b) a permeation tube extending across said chamber, said tube being formed from a material which is permeable to said at least one gaseous pollutant, a first end of said permeation tube being connected to a source of pure pressurized vector gas and a second end of said tube being fluidically connected to a mixer, said mixer being connected to a source of dilution zero air;
    (c) means for regulating the temperature within said permeation chamber, said temperature regulating means thus comprising means for maintaining a predetermined constant temperature within said permeation chamber, said permeation chamber being substantially cylindrical and having two end faces, said end faces comprising inlet and outlet unions, respectively; and
    (d) metal tubes locked by nuts, said metal tubes extending through respective ones of said inlet and outlet unions, said metal tubes extending coaxially within said cylindrical chamber and having ends which are welded to an intermediate tube having a smaller diameter, said intermediate tube being formed from stainless steel and being pierced over at least a portion of its length by a plurality of holes, said permeation chamber extending around said intermediate tube.

2. A calibration system in accordance with claim 1, said permeation chamber being positioned within a heat-regulated enclosure, said heat-regulated enclosure having a substantially constant temperature, said system further comprising an electrical temperature regulating device for maintaining the temperature within said enclosure substantially constant.

3. A calibration system in accordance with claim 2 wherein the temperature within said heat-regulated enclosure is approximately equal to 64° C.

4. A calibration system for gas analyzers which is adapted for use with apparatus for measuring atmospheric pollution and for detecting gaseous pollutants, said calibration system comprising a sealed permeation chamber connected to a source of at least one gaseous pollutant, a permeation tube extending across said chamber, said permeation tube being formed from material which is permeable to said at least one gaseous pollutant, said permeation tube having one end which is connected to a cylinder of pressurized pure vector gas, said system further comprising means for regulating the temperature within said permeation chamber and for maintaining a predetermined constant temperature within said permeation chamber, said permeation tube being connected at its other end to a first three-way valve which comprises means for communicating said permeation chamber with a reaction chamber, said three-way valve being fluidically connected to a sampling mixer, said mixer being connected to a source of dilution zero air, said reaction chamber being attached to said sampling mixer, said sampling mixer comprising a plurality of outlet connectors which are adapted to be connected to a plurality of gas analyzers and a pipe for evacuating excess mixture from said mixer, said system further comprising a circuit for conducting dilution zero air, said circuit including a filter connected to one end of a coil, said coil and said permeation chamber being positioned within a heat-regulated enclosure, said coil being fluidically connected to an ozone generator, said ozone generator being fluidically connected to an intake orifice of a pump via a pipe connected to an active charcoal filter, said pump having a delivery orifice which is connected at one end to said sampling mixer to comprise means for providing a flow of dilution gas and at a second end via a second three-way valve to a quartz tube which extends across said ozone generator, said second three-way valve comprising means for selectively short-circuiting said quartz tube in said ozone generator.

5. A calibration system in accordance with claim 4 further comprising means for regulating the rate of flow of zero dilution air to said sampling mixer and said ozone generator to maintain the rate of flow to said sampling mixer at a substantially greater value than the rate of flow to said ozone generator.

* * * * *